United States Patent [19]

Cushman

[11] 4,194,121

[45] Mar. 18, 1980

[54] METHOD AND APPARATUS FOR PROVIDING SIMULTANEOUS DISPLAYS IN PANORAMIC RADIOGRAPHY

[75] Inventor: Robert H. Cushman, Princeton, N.J.

[73] Assignee: Pennwalt Corporation, Philadelphia, Pa.

[21] Appl. No.: 969,042

[22] Filed: Dec. 13, 1978

[51] Int. Cl.² ............................................. G03B 41/16
[52] U.S. Cl. ................................. 250/439 P; 250/468
[58] Field of Search ............... 250/439 R, 439 P, 444, 250/445 R, 446, 447, 448, 449, 468, 490, 320, 323

[56] References Cited

U.S. PATENT DOCUMENTS 3,636,349   1/1972   Faude ............................... 250/439 P Primary Examiner—Craig E. Church
Attorney, Agent, or Firm—Arthur M. Suga

[57] ABSTRACT

Two different areas of a focal trough of a dental arch structure are simultaneously displayed on a radiograph when tubehead-camera assembly of an X-ray machine panoramically scans the dental arch structure. The different areas of the focal trough are obtained when a pair of parallel disposed film holding devices within the camera are caused to travel in proximate relationship to each other at different speeds. The X-rays activate and pass through one film before activating the other immediately therebehind.

5 Claims, 7 Drawing Figures

METHOD AND APPARATUS FOR PROVIDING SIMULTANEOUS DISPLAYS IN PANORAMIC RADIOGRAPHY

STATEMENT OF THE INVENTION

The present invention relates to radiography and more particularly to the provision of simultaneous displays of different areas of a dental arch focal trough.

CROSS-REFERENCE TO RELATED APPLICATIONS

Reference is hereby made to the following copending patent application:

Ser. No. 889,708, filed Mar. 24, 1978, for "Film Drive Mechanism for Panoramic Dental X-Ray Machine", of A. Ciavattoni et al. assigned to the present assignee.

BACKGROUND AND SUMMARY OF THE INVENTION

Prior art panoramic dental X-ray machines are well known. Some provide a continuous image of the dental arch area and commonly employ an X-ray source and X-ray film both optically aligned with each other and supported on a rotatable carrying arm which orbits a patient situated in the path of the X-ray beams. The patient may remain stationary or be transported in a patient chair in accordance with various type drive mechanisms in order to simulate the generally elliptical shape of the human dental arch. The continuous image radiograph provides the dentist with a panoramic view of the teeth and associated structures and is therefore a useful diagnostic aid in many phases of dental practice.

Various other prior art apparatus provide a discontinuous, or split image panoramic radiograph which possesses certain advantages. Here, the dentist is presented with additional interpretive information since two distinctly different views of the incisors, or centrals area are provided. Additionally, overlying spinal shadows which would be cast over the central-bicuspid region are eliminated since X-rays are not generated when the spine is aligned with the X-ray source and film.

Regardless of the type radiographic image to be obtained, i.e., continuous or discontinuous, compensation is usually made for the fact that the curvature of the desired area of focus is generally not a true circle or ellipse. Thus, the rate of film travel must be varied in accordance with the rate of travel of the X-ray source about the patient's head in order that the radiological projections occupy a distance on the film equal to the linear distance of a curved structure being X-rayed, such as a typical dental arch.

In U.S. Pat. No. 2,798,958, apparatus is disclosed for varying the rate of film travel relative to the rate of travel of the X-ray source. The X-ray source and film carrier are both supported by a single member permitting both the X-ray source and film carrier to orbit the patient at an uniform rate of travel. Means are also disclosed for reorienting the patient after completion of one-half of the excursion cycle in order to relocate the center of the axis of rotation with respect to the patient's head prior to X-raying the other one-half of the dental arch in order to provide the discontinuous, or split radiographic images.

In U.S. Pat. No. 3,045,118, apparatus is disclosed which automatically shifts the patient in order that the line of sight between the X-ray source and film bypasses the patient's spinal column and permits X-raying of the other half of the dental arch. Apparatus is also disclosed therein for continuously moving an X-ray source and extraoral film holder about the patient.

In U.S. Pat. No. 3,636,349, assigned to the present assignee, structure is disclosed for revolving the X-ray source and film carrier about the head of a patient who remains fixed in position while the center-line of the orbit continuously moves through an arcuate path approximating the arch of the patient's teeth. The patent further discloses film carrier means which may be used advantageously in the practice of the present invention.

Thus, the prior art discloses various types of structures, apparatus and mechanism for orbiting the X-ray source-X-ray film (tubehead-camera) assemblies in circular or arcuate paths; for varying film travel speed in accordance with tubehead-camera assembly movements; for shifting the patient in a chair; and for providing continuous or discontinuous type radiographic images.

In panoramic radiography, a selected layer of the dental arch structure is in sharp focus, called the focal trough, which is in a vertical curved plane having a horizontal dimension or width designed to portray radiographically part of the bone of the maxilla, part of the bone of the mandible, and the teeth. Present day continuous panoramic systems each suffer from an inherent infirmity of providing a radiograph having an extremely narrow focal trough width in the central region (incisors). This narrow focal trough width in the centrals is a serious limitation since it is virtually impossible to display both the incisal edge of the central teeth as well as their root areas, resulting in less available diagnostic information.

The present invention is capable of providing two simultaneous displays of two different focal trough areas at the centrals, or any different areas of the focal trough by means of a camera assembly containing two films which travel at different speeds past the camera slot and wherein only one exposure of the patient is required, markedly reducing the radiation dosage required.

DETAILED DESCRIPTION OF THE INVENTION

Figure 1:
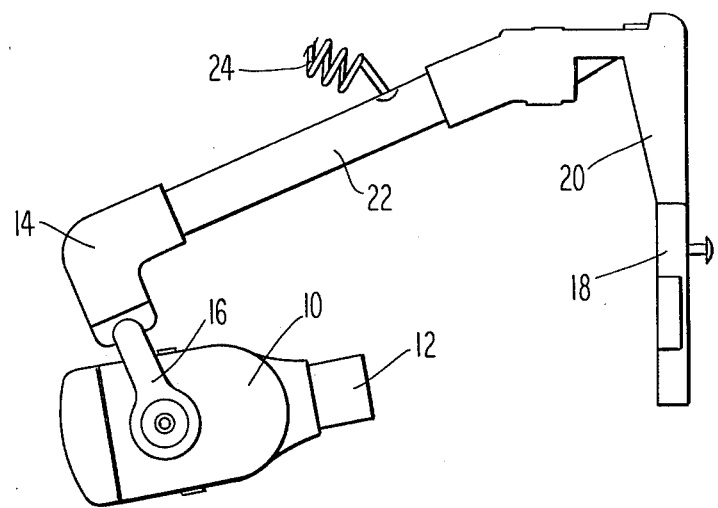
FIG. 1 is an assembly view of a tubehead-camera assembly of a prior art panoramic dental X-ray machine.

In FIG. 1, tubehead 10 includes cone 12 which focuses X-rays generated by an X-ray source within the tubehead. Trunnion 14 carries yoke 16 which permits limited tubehead rotation. A cassette holder assembly or camera 18 contains X-ray film to be activated by the X-ray source. Camera 18 is supported by camera support 20 which receives one end of horizontal arm 22, its other end received by trunnion 14. Horizontal arm 22 and camera support 20 maintain tubehead 10 and camera 18 a specified distance from each other and in alignment with the patient's head as they rotate about the patient. Power is supplied to the X-ray source through cable 24. The entire assembly above described is supported by assembly support arm 26, shown in FIG. 2. Assembly support arm 26 is received by a bifurcated casting 28 having a pair of vertically aligned holes 30—30 which receive output shaft 32 of a shaded pole motor (not shown). Shaft 32 rotates at a slow uniform speed.

Camera 18 is conventional, except as modified, later described. It comprises cassette holder 40, cassette carriage 42 which travels within the cassette holder along rollers 44 when cable 46 and retrieving spring 48 cooperate, through cable roller 50 and other means, to move cassette carriage 42 and its film past vertical slit diaphragm or slot 52 disposed centrally the front panel of the camera. Slot 52, of course, permits the generated X-rays to pass therethrough for activation of X-ray film 54 carried by cassette carriage 42. Slot 52 also prevents scatter radiation from entering the camera assembly to cause image deterioration. Hinges 55 permit door 56 to be opened for gaining access to the interior of camera 18. Door 56 is provided with a lead shield (not shown) aligned with tubehead 10 and slot 52.

Figure 2:
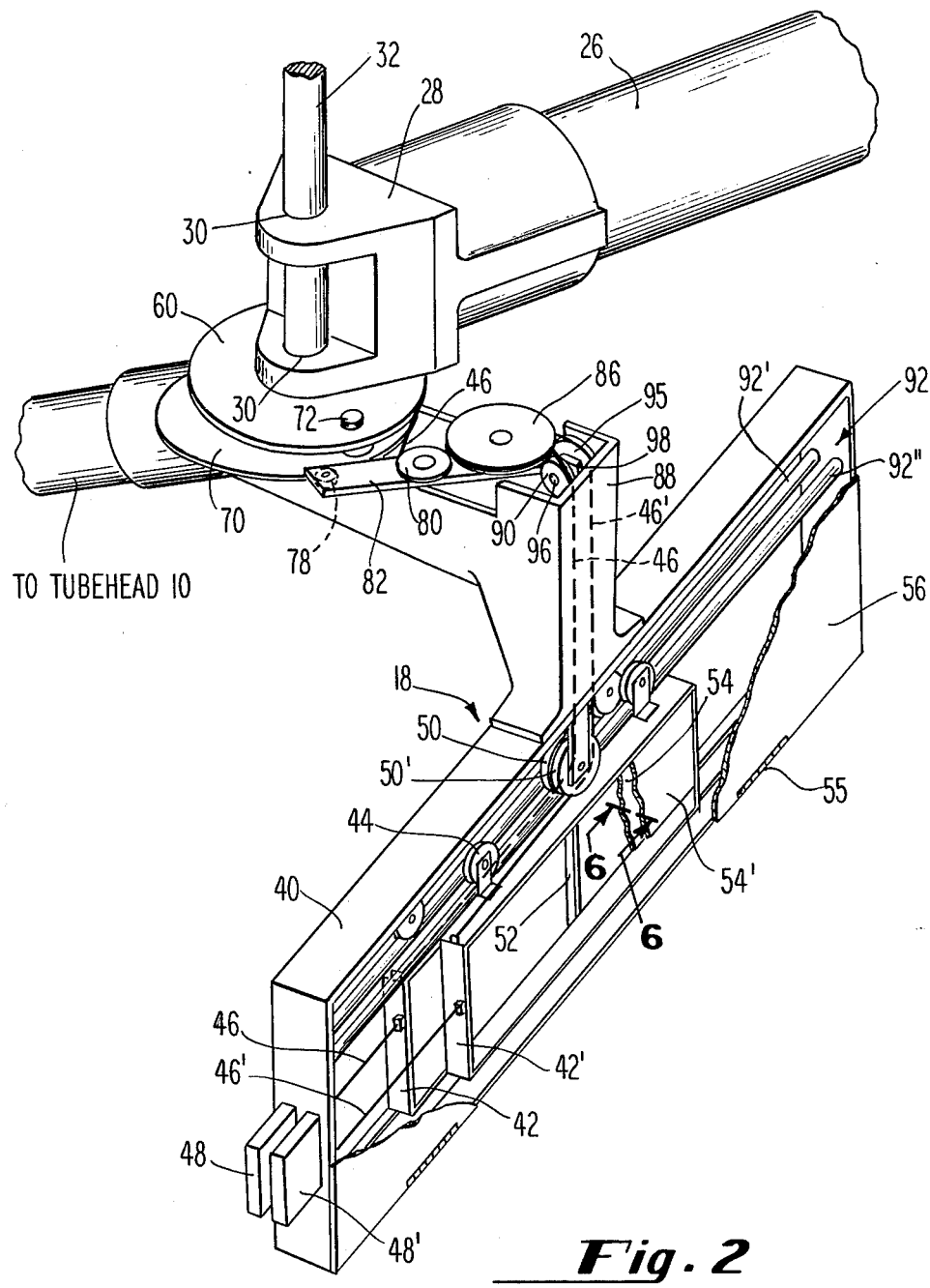
FIG. 2 is a perspective view of the assembly of FIG. 1, modified in accordance with the present invention.
Figure 3:
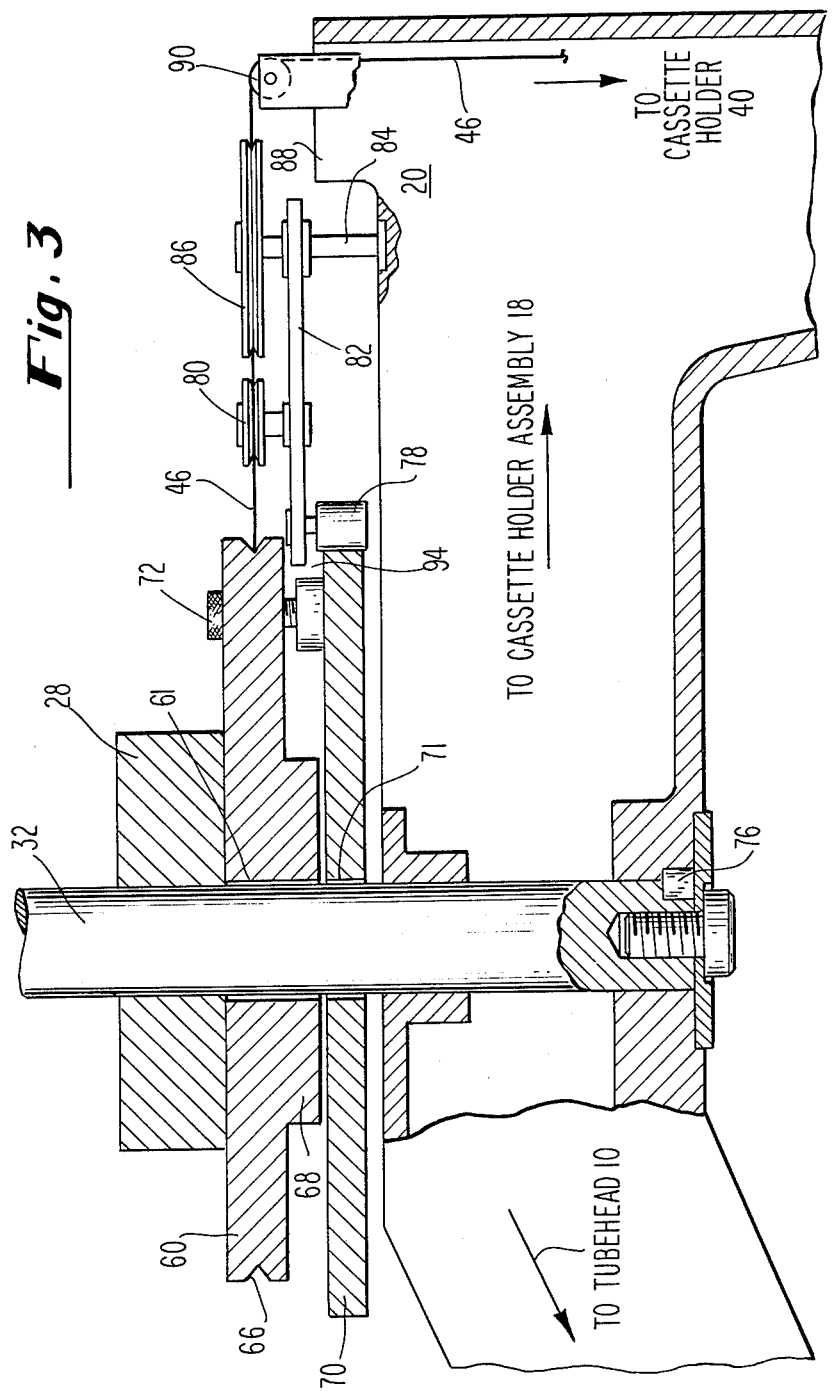
FIG. 3 is a partially sectioned elevational view of a portion of the mechanism depicted in FIG. 2.
Figure 4:
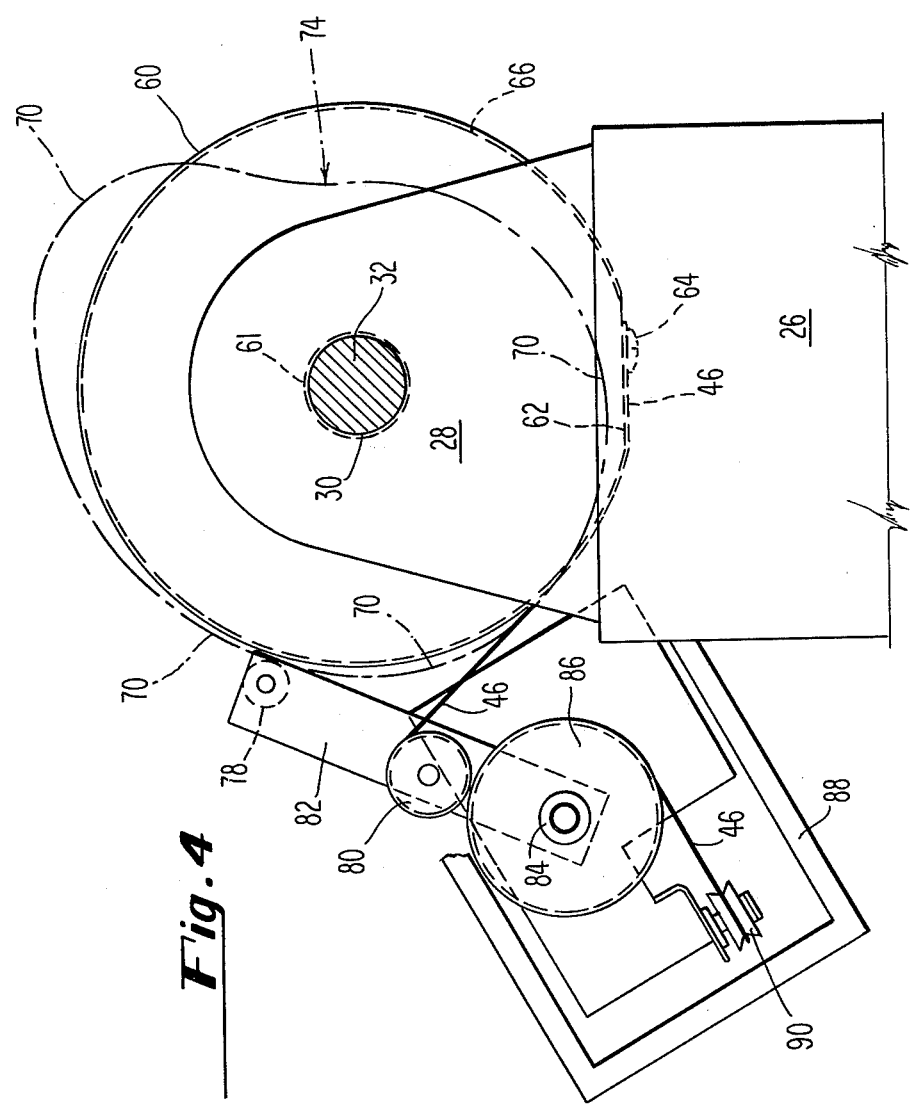
FIG. 4 is a plan view of film drive mechanism of FIG. 2.

Referring to FIGS. 2, 3 and 4, storage disc 60 has a flattened edge 62 at a rear portion thereof. Storage disc 60 is fixedly mounted to casting 28 by suitable means (not shown). Cable 46 is secured to storage disc 60 at flattened edge 62 by cable connector 64. Storage disc 60 is provided with a circumferential groove 66 for maintaining cable 46 on the storage disc during rotation of tubehead 10 and cassette holder assembly 18 by shaft 32. Storage disc 60 is also provided with a spacer 68, either formed integrally therewith, or otherwise suitably affixed thereto. Function of spacer 68 is later described.

A cam 70 is disposed below storage disc 60 and is secured in operating position by means of a cam adjustment screw 72. By loosening screw 72, cam 70 may be rotated around shaft 32 for purposes for adjustment. Cam 70 is provided with cam surfaces shown generally at 74 for controlling the speed of film travel.

Storage drum 60 and cam 70 do not rotate with shaft 32. Storage drum 60 and cam 70 have oversized bores 61 and 71 respectively which provide clearances for shaft 32 to rotate therewithin. Tubehead 10 and camera 18 rotate with shaft 32 through conventional key means 76. A cam follower 78 and V-guide roller 80 are rotatably mounted to opposite surfaces of a plate 82. Plate 82 is pivotally mounted about roller shaft 84 of another V-guide roller 86 which is pivotally mounted to an upper surface 88 of camera support 20. Cassette holder assembly support 20 mounts a pulley 90.

In assembling cable 46 to the film drive mechanism, one end is secured to the storage disc at flattened edge 62. The cable is then threaded around the V of roller 80 in a counterclockwise direction (when viewed from above). Roller 86 is then similarly threaded, but in a clockwise direction, before threading into cassette holder 40 around pulley 90. Retrieving spring 48 receives the other end of cable 46.

Thus, by means of the mechanism described, follower 78 is constantly urged against cam 70, including its cammed surfaces, when tubehead 10 and camera 18 rotates about the patient.

Spacer 68 permits plate 82 to enter space 94 immediately below storage disc 60 when follower 78 is urged inwardly, or toward shaft 32. Absent space 94, plate 82 would contact storage disc 60 to prevent follower 78 from continuously following the working surfaces of cam 70.

Referring again to FIG. 2, camera assembly 18 is further modified in accordance with the present invention to include an additional cassette carriage 42', rollers 44', cable 46', retrieving spring 48', cable roller 50' and film 54', each of which is substantially identical with its counterpart. Rod 92 is provided with dual tracks 92' and 92'' to permit cassette carriages 42 and 42' respectively to travel independently of each other on rollers 44 and 44' respectively. Each of films 54 and 54' is positioned within its respective cassette carriage to be in very close proximity with the other while the cassette carriages are moving at different speeds. The difference in the speed of travel of each cassette carriage is determined by the difference in diameters of pulley 90 and spool 95. Cable 46' is secured for rotation around spool 95 and cooperates with the components associated with cassette carriage 42'. Pulley 90 and spool 95 are both fixedly mounted on shaft 96 which rotates within a mounting member 98. Spool 95 is sufficiently wide to receive many windings of cable 46' therearound without danger of overlapping. Cable 46' is attached to spool 95 only.

In operation, larger diameter spool 95 will cause cable 46' to travel faster than cable 46 to thereby move cassette carriage 42' at a faster rate of travel than cassette carriage 42. Thus, by merely varying the diameter of spool 95, different ratios of travel of the cassette carriages are obtained, which ratios and diameters are calculable and predictable by a mathematician and may be controlled or adjusted in accordance therewith.

Figure 5:
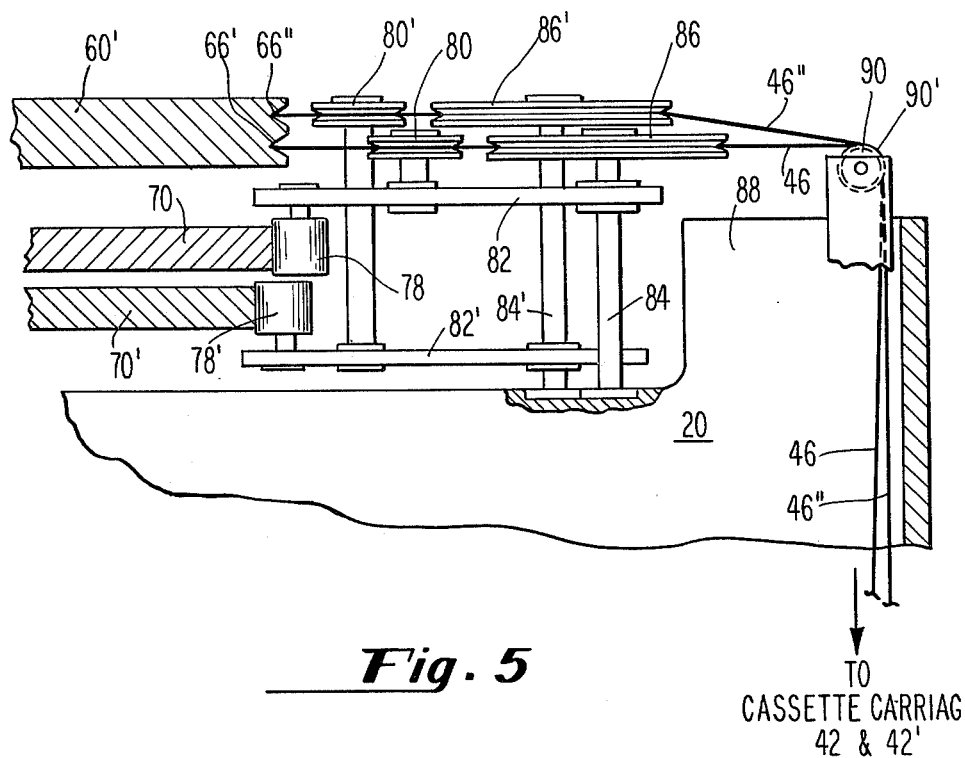
FIG. 5 is a view similar to FIG. 3 showing two cams for providing two different film speeds.

In FIG. 5, a pair of non-identical cams 70 and 70' are provided, the lower cam 70' cooperating with cam follower 78', V-guide rollers 80' and 86', plate 82', roller shaft 84'; and pulley 90', identical with pulley 90, each pulley mounted for rotation independently of the other on shaft 96. Storage drum 60' is provided with a pair of circumferential grooves 66' and 66'' for releasably storing cables 46 and 46'' respectively, which cables effect movement of cassette carriages 42 and 42' respectively. Thus, whereas the ratios between the focal troughs are substantially fixed when the apparatus of FIG. 3 is used, a variable ratio is readily obtainable by merely varying cam configurations in the modification illustrated in FIG. 5. Plates 82 and 82' are sufficiently distant from each other to prevent their interference with each other during operation. Cams 70 and 70' may be suitably clamped together after adjustment thereof before tightening cam adjustment screw 72 of FIG. 3 (not shown in FIG. 5), or other suitable means may be used for securing the adjusted cams in place if they are spaced from each other as shown in FIG. 5.

Figure 6:
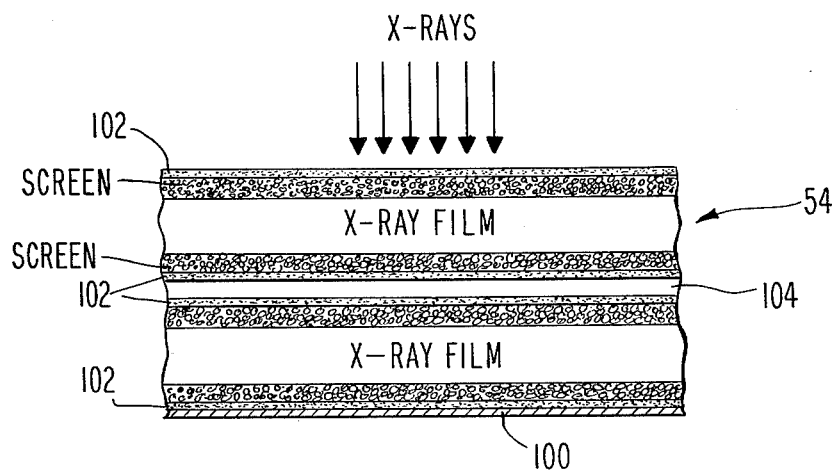
FIG. 6 is a sectional view of the films illustrated in FIG. 2 taken along line 6—6 thereof.

In FIG. 6, films 54 and 54' are identical. An attenuating lead layer 100 however is disposed immediately behind film 54' only. Each surface of each X-ray film is in contact with a phosphor intensifying screen, which, in turn, is coated with a protective layer 102. The screens and protective layers are conventional. An air space 104 is provided between the films and permits relative movement of the cassette carriages with no interference from the other.

Figure 7:
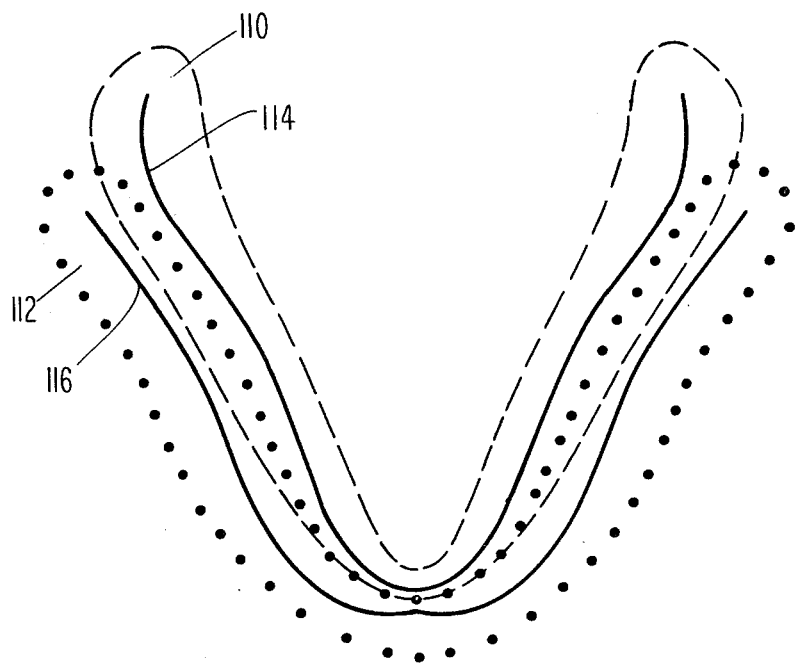
FIG. 7 illustrates two different focal trough areas of a dental arch structure displayed simultaneously.

In FIG. 7, two focal trough areas 110 and 112 are simultaneously displayed, represented by dashed and dotted lines respectively, having respective solid line center lines 114 and 116. Focal trough areas 110 and 112 were obtained using pulleys 90 and 95 respectively, the latter causing cassette carriage 42' to travel 20% faster than cassette carriage 42.

The invention is not intended to be limited to structure herein disclosed for providing varying cassette carriage speed ratios. For example, rotary motion flexible shafts, gearing, servomechanisms, or combinations thereof, or other suitable means are contemplated by the present invention.

I claim:

1. A process for providing a plurality of simultaneous panoramic displays of different portions of focal trough of dental arch area of a patient by means of a tubehead-camera assembly continuously orbiting about said patient, said process comprising
    irradiating said dental arch area of said patient with radiation from an X-ray source within said orbiting tubehead to produce intelligence carrying radiation,
    directing said intelligence carrying radiation while said tubehead and camera are orbiting about said patient onto a first recording medium moving within said orbiting camera at a predetermined speed,
    permitting said radiation directed onto said first recording medium to activate said first recording medium before substantially passing therethrough for activating a second recording medium immediately rearwardly said first recording medium,
    said second recording medium moving within said orbiting camera at a speed dissimilar to said speed of said first recording medium.

2. The process as described in claim 1 wherein said intelligence carrying radiation is directed through a slot in said camera.

3. The process as described in claim 2 wherein said second recording medium is moving within said orbiting camera at a speed about 20% faster than speed of said first recording medium.

4. In a panoramic dental X-ray machine having a tube-head-camera assembly including a tubehead containing an X-ray source and a camera for holding X-ray film to be activated by said X-ray source, said tubehead-camera assembly continuously orbiting about dental arch structure of a patient for panoramic radiographing thereof, the combination therewith of the improvement for providing simultaneous displays of different areas of focal trough associated with said dental arch structure, said improvement comprising
    a pair of cassette carriages disposed in proximate relationship within said camera and adapted for similar parallel motion at differing speeds,
    cable means associated with each of said cassette carriages for effecting said differing speed parallel motion, and
    cooperating pulley and spool means mounted externally said camera for moving said cable means at differing speeds, said pulley and spool means having different diameters and controlled for simultaneous rotation by a common source.

5. In a panoramic dental X-ray machine having a tubehead-camera assembly including a tubehead containing an X-ray source and a camera for holding X-ray film to be activated by said X-ray source, said tubehead-camera assembly continuously orbiting about dental arch structure of a patient for panoramic radiographing thereof, the combination therewith of the improvement for providing simultaneous displays of different areas of focal trough associated with said dental arch structure, said improvement comprising
    a pair of cassette carriages disposed in proximate relationship within said camera and adapted for similar parallel motion at differing speeds,
    a pair of non-identical cam means mounted on said machine externally said camera in operable association with said pair of cassette carriages,
    cable means communicating between said cam means and said cassette carriages for effecting said differing speed parallel motion of said cassette carriages.

* * * * *